(12) United States Patent
Lee

(10) Patent No.: US 6,322,572 B1
(45) Date of Patent: Nov. 27, 2001

(54) THROMBUS MACERATOR CATHETER

(75) Inventor: Jeffrey A. Lee, Plymouth, MN (US)

(73) Assignee: NeuroVasx, Inc., Maple Grove, MN (US)

( * ) Notice: Subject to any disclaimer, the term of this patent is extended or adjusted under 35 U.S.C. 154(b) by 0 days.

(21) Appl. No.: 09/371,267

(22) Filed: Aug. 10, 1999

(51) Int. Cl.$^7$ .................................................. A61D 1/02
(52) U.S. Cl. ............................................................ 606/159
(58) Field of Search ...................................... 606/127, 128, 606/159, 170, 167, 171; 600/564

(56) References Cited

U.S. PATENT DOCUMENTS

| 5,554,163 | * | 9/1996 | Shturman | 606/107 X |
| 5,584,843 | * | 12/1996 | Wulfman et al. | 606/159 |
| 5,843,103 | * | 12/1998 | Wulfman | 606/159 |
| 5,954,737 | * | 9/1999 | Lee | 606/159 |
| 6,090,118 | * | 7/2000 | McGuckin, Jr. | 606/159 |

FOREIGN PATENT DOCUMENTS

| 533321 | * | 12/1977 | (EP) | 606/159 |
| 584856 | * | 12/1977 | (SU) | 606/159 |
| 665908 | * | 6/1979 | (SU) | 606/159 |

* cited by examiner

*Primary Examiner*—Jeffrey A. Smith
(74) *Attorney, Agent, or Firm*—Schwegman, Lundberg, Woessner & Kluth, P.A.

(57) ABSTRACT

The present invention includes a thrombus disrupting device. The device comprises a main body that defines a lumen comprising a distal end portion. A wire is positioned within the lumen and extends from the lumen. The wire comprises a distal end. The device also comprises a main body segment defining the lumen, the main body segment positioned over the wire, proximal to the distal end of the wire and distal to the main body. The wire has a first arc conformation wherein the main body segment is separated from the main body and a second arc-free conformation wherein the main body segment contacts the main body.

6 Claims, 8 Drawing Sheets

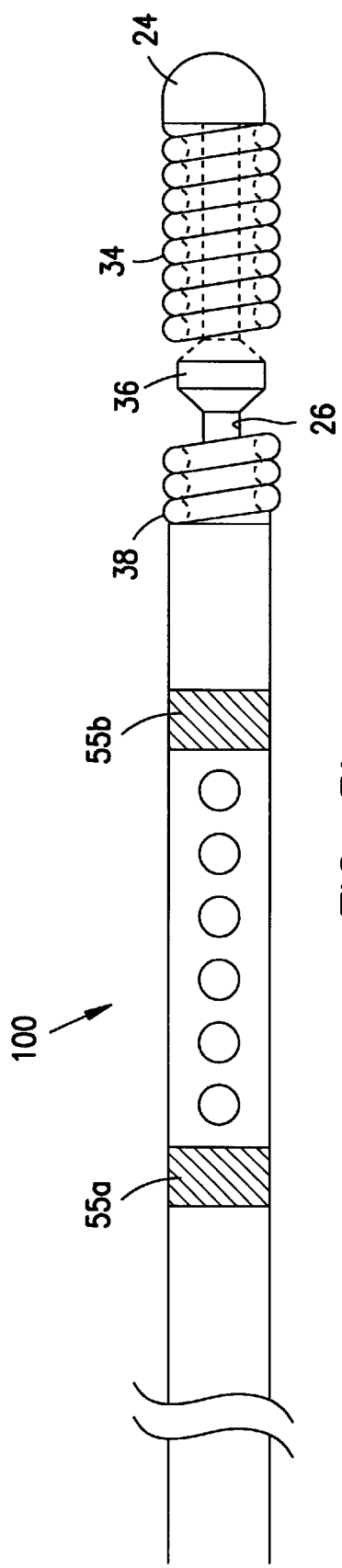
FIG. 5b
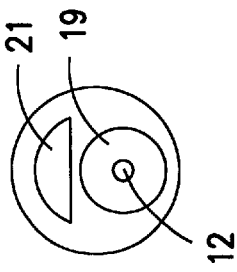
FIG. 5d2
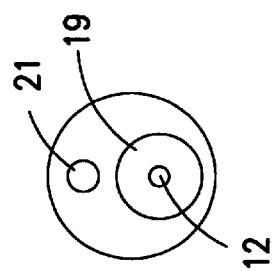
FIG. 5d1
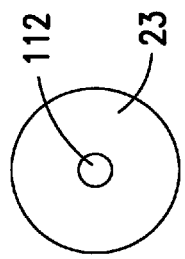
FIG. 5C

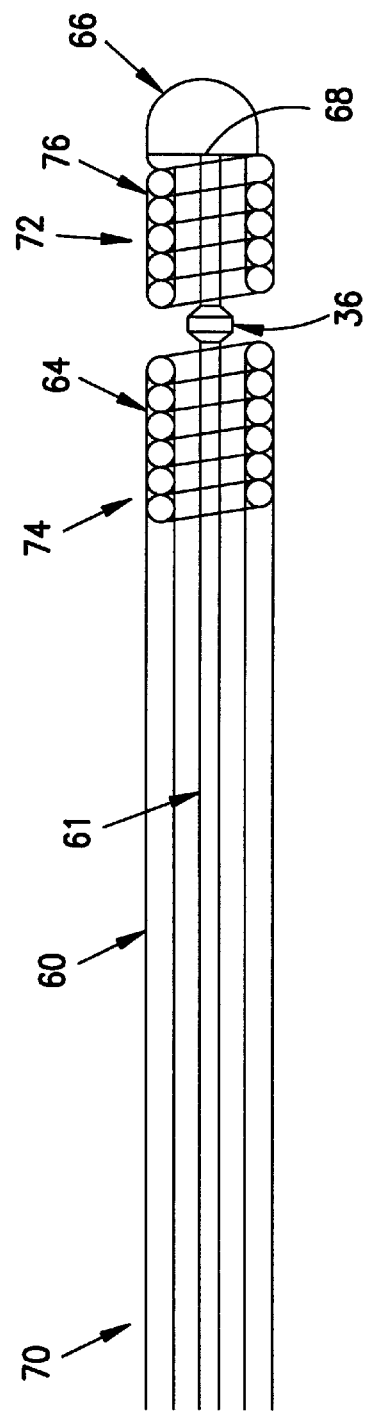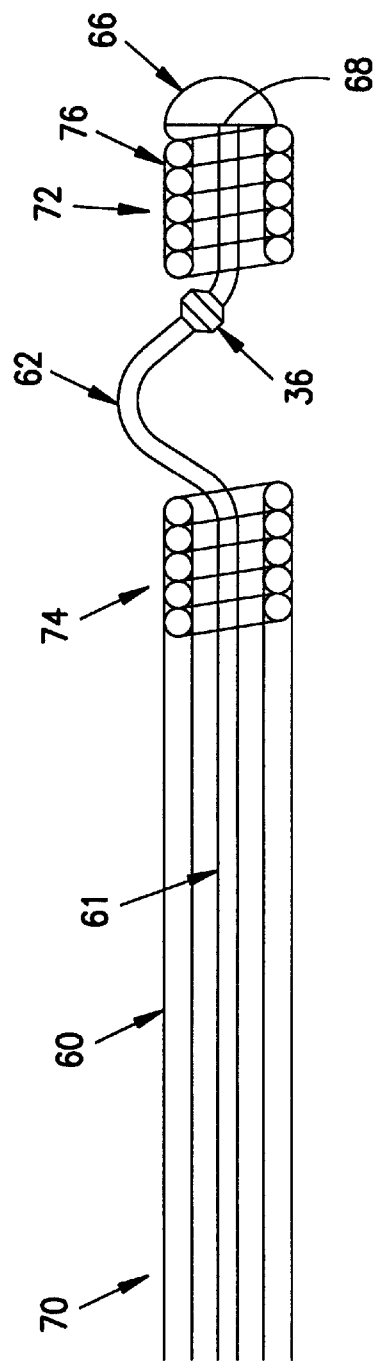

THROMBUS MACERATOR CATHETER

BACKGROUND OF THE INVENTION

The present invention relates to a catheter or to a microcatheter or to a guidewire for macerating a thrombus and to a method for thrombus maceration with the catheter or the microcatheter or the guidewire.

Guidewires have had use in procedures such as percutaneous transluminal coronary angioplasty (PTCA), and as mechanisms for advancing a catheter to a treatment site within a blood vessel. In one type of procedure, a guiding catheter is introduced into a patient's arterial system and is advanced to an ostium of the patient's diseased artery. A guidewire has been used with the guiding catheter in over-the-wire procedures wherein the guidewire is preloaded with an inner lumen of a dilatation catheter. Both the dilatation catheter and the guidewire are advanced through the guiding catheter to a distal end of the guiding catheter. The guidewire is advanced out of the distal end of the guiding catheter into the artery.

A physician may shape the distal end of the guidewire to facilitate guiding it through coronary anatomy to a diseased region. When the guidewire is in a desired position, the dilatation catheter is advanced out of the guiding catheter over the guidewire where it may be activated when properly positioned.

Guidewires may be fixed or may be built in to a steerable catheter. Guidewires typically include an elongated core member with a flexible helical coil secured to a distal extremity of the core member. The core member can extend to the distal end of the coil and can be secured thereto. Alternately, the distal extension of the core element can terminate short of the distal end of the coil and a shaping ribbon can extend to the distal end of the coil and can be secured by its distal end thereto. The ribbon may be secured by soldering or brazing to the core element.

The Kotula et al. Pat. U.S. No. 5,569,275, issuing Oct. 29, 1996, describes a thrombus macerating device that includes an elongate, flexible shaft which can be guided along a vascular path. A rotor or impeller with blades is affixed to the shaft adjacent to its distal end. A drive mechanism is provided for rotating the shaft and the rotator which is attached to the shaft. The rotor is retained within a rotor housing and rotates within the housing. The rotor housing includes a cylindrical wall that surrounds the rotor and that has at least three ports spaced angularly about the circumference of the housing. As the rotor is rotated, it will tend to draw blood into the housing in a proximal direction and expel the blood out through the ports. The blood then tends to be drawn back into the distal end of the housing and through the rotor again. This movement sets up a recirculating vortex which repeatedly passes the blood across the blades.

When the blood is ejected through the ports in the housing within a vascular channel, the blood will act against the wall of the channel. This action maintains the housing in a position which is faced away from the surrounding vascular wall. By spacing the ports angularly about the circumference of the housing, the force exerted by the ejected blood tends to maintain the housing and rotor carried within the housing in a position that is centered within a vascular channel.

The Kotula et al. Pat. U.S. No. 5,284,486, issuing Feb. 8, 1994, describes a mechanism for breaking down a thrombus with rotating blades. The thrombus is broken down into particles which are fine enough to be left in the vascular system without a significant risk of forming additional thrombi. The mechanism also includes another mechanism to ensure that rotating blades of the mechanism do not directly contact walls of a vessel, but remain centered within the vessel. The mechanism includes an elongate, flexible shaft with a rotor or impeller having blades affixed to the shaft adjacent its distal end. A drive mechanism is provided for rapidly rotating the shaft and the rotor attached to the shaft. The rotor is retained within a rotor housing and rotates within the housing. The rotor housing includes a generally cylindrical wall that is substantially surrounding the rotor and that has at least three ports spaced angularly about the circumference of the housing. As the rotor is rotated, it will tend to draw blood into the housing in a proximal direction and expel the blood out through the ports. The blood then tends to be drawn back into the distal end of the housing and through the rotor again. This activity sets up a recirculating vortex which repeatedly passes the blood across the blades.

The thrombus may also be dissolved because the thrombus is comprised of components that can be dissolved or "lysed" with drugs such as TPA and Urokinase. In conventional stroke therapy, TPA is administered via a systemic intravenous (I.V.) Administration. The drugs are infused throughout the entire circuitry system so that only a very diluted concentration of drug actually contacts the thrombus.

SUMMARY OF THE INVENTION

One embodiment of the present invention includes a thrombus disrupting device. The device comprises a main body. The main body defines a lumen that comprises a distal end portion. A wire is positioned within the lumen and extends from the lumen. The wire comprises a distal end. The device also includes a main body segment that defines the lumen. The main body segment is positioned over the wire, proximal to the distal end of the wire and distal to the main body. The wire has a first arc conformation wherein the main body segment is separated from the main body and a second arc-free conformation wherein the main body segment contacts the main body.

Another embodiment of the present invention includes a thrombus disrupting device. The thrombus disrupting device comprises an elongated tubular main body and a wire positioned within the tubular main body. The wire, in one position, defines an arc. The arc is proximal to the distal end of the wire.

Another embodiment of the present invention includes a guidewire. The guidewire comprises an elongated wire-based main body with a distal end and a proximal end. The main body comprises an endcap at its distal end and is memory shaped proximal to its distal end to form at least one arc. A cover segment is positioned over the main body and is positioned adjacent the endcap and the arc.

Another embodiment of the present invention includes a method for disrupting a thrombus. The method comprises providing a wire with a first arc shape and a second straight shape. The wire is positioned within a thrombus when the wire has the arc shape. The wire is transversely moved so that the arc moves back-and-forth within the thrombus, or rotated within the thrombus.

One other embodiment of the present invention includes a core wire. The core wire comprises a proximal wire portion and a distal memory-shaped portion. The distal memory-shaped portion is memory shaped to have at least one arc. The distal memory-shaped portion has a second, straightened arc-free symmetry. In another embodiment, the core wire includes a stop mechanism.

Another embodiment of the present invention includes a catheter assembly. The catheter assembly includes a main body that defines a lumen and a thrombus disrupting device positioned within the lumen. The thrombus disrupting device comprises an elongated tubular main body with a distal end and a wire positioned within the tubular main body. The wire, in one position, defines an arc. The arc is proximal to the distal end.

BRIEF DESCRIPTION OF THE DRAWINGS

FIG. 5b illustrates a side view of one embodiment of an infusion catheter with another embodiment of the macerating component of the present invention.

FIG. 5c illustrates a cross-sectional view of one embodiment of a single lumen EHIC catheter.

FIG. 5d1 illustrates a cross-sectional view of one embodiment of a duel lumen EHIC catheter.

FIG. 5d2 illustrates a cross-sectional view of one other embodiment of a duel lumen EHIC catheter.

FIG. 6a illustrates a side view of one embodiment of a guidewire that comprises an arc for maceration of a thrombus wherein the arc is straightened.

FIG. 6b illustrates a side view of one embodiment of the guidewire that comprises the arc for maceration of a thrombus.

DETAILED DESCRIPTION OF EMBODIMENTS

Figure 1:
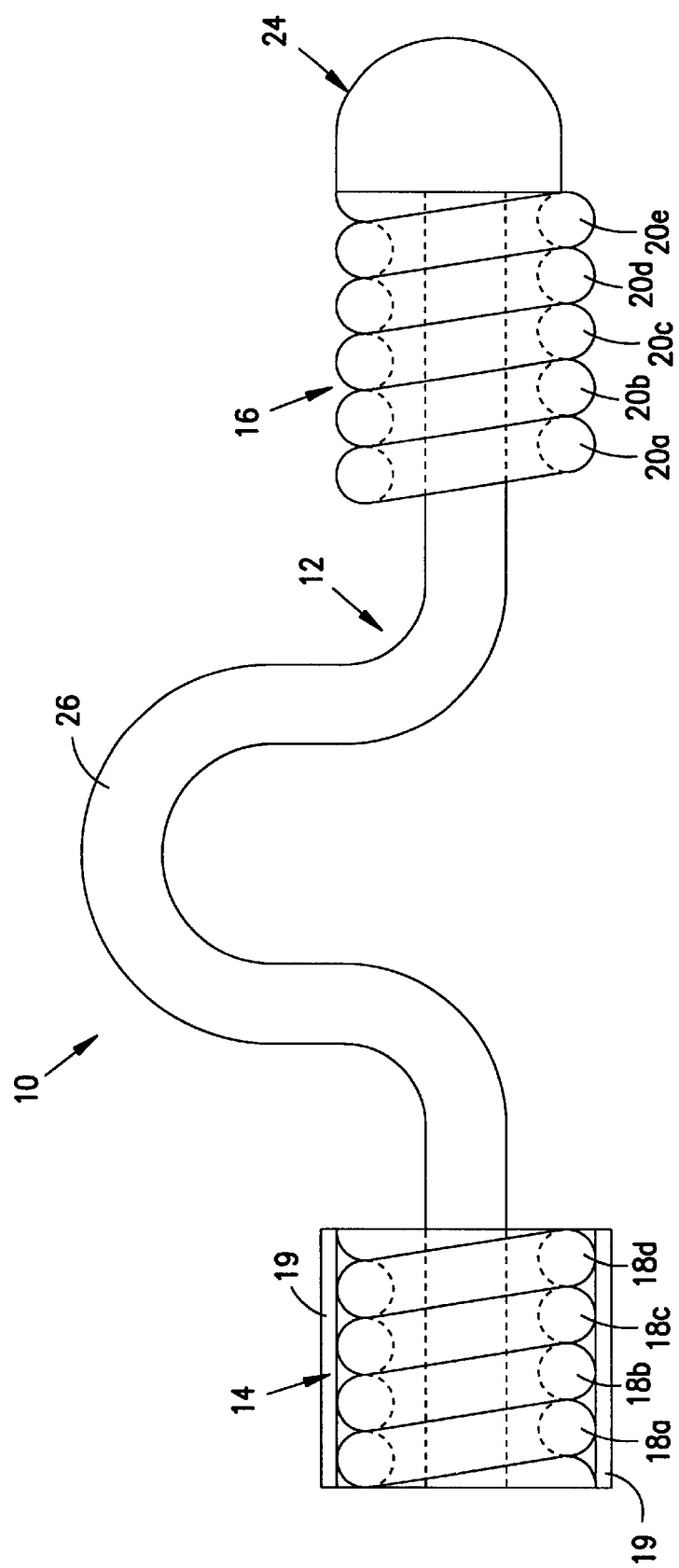
FIG. 1 illustrates a side view of one embodiment of the thrombus macerator of the present invention with a macerator component in an expanded, activated position.

One embodiment of the thrombus macerator catheter of the present invention, illustrated generally at 10 in FIG. 1, comprises a catheter body illustrated as comprising proximal portion 14 and distal portion 16 in FIG. 1 and a core wire 12 that is slidably positioned within the catheter portion 14 attached to 16, as shown in FIG. 1. The proximal main body portion 14 is comprised of a plurality of coiled segments 18 a, b, c, and d. The distal main body portion 16 is comprised of coiled segments 20 a, b, c, d, and e. While coiled segments 18a, b, c and d are shown, it is understood that coiled segments 18 extend to a proximal end of the catheter 10. The coiled segments 18 are, in one embodiment, covered with a flexible sleeve 19. While coiled segments are shown, it is understood that other conventional flexible coverings are suitable for use in the present invention.

The distal catheter portion 16 terminates at an endcap 24 defined by the core wire 12. Distal segment 16 is made of radiopaque materials and has a radiopaque coating or covering.

The coiled segments 18a–d and 20a–e are made, in one embodiment, of wire or filament. The wire may be flat, square, round, half-round or triangular in cross-section. The wire or filament may be made from biocompatible materials such as platinum, palladium, rhodium, gold, silver, tungsten, iridium, nickel-titanium alloys, Elgiloy, various stainless steels as well as materials coated with a biocompatible coating. Suitable biocompatible polymers for use as wire or filament in the coils include polyethylene, polyurethane, polyester, and polypropylene. It is also believed that polymers such as nylon, Teflon and inorganic materials such as fibrous carbon are also suitable for use as coil material.

Figure 4:
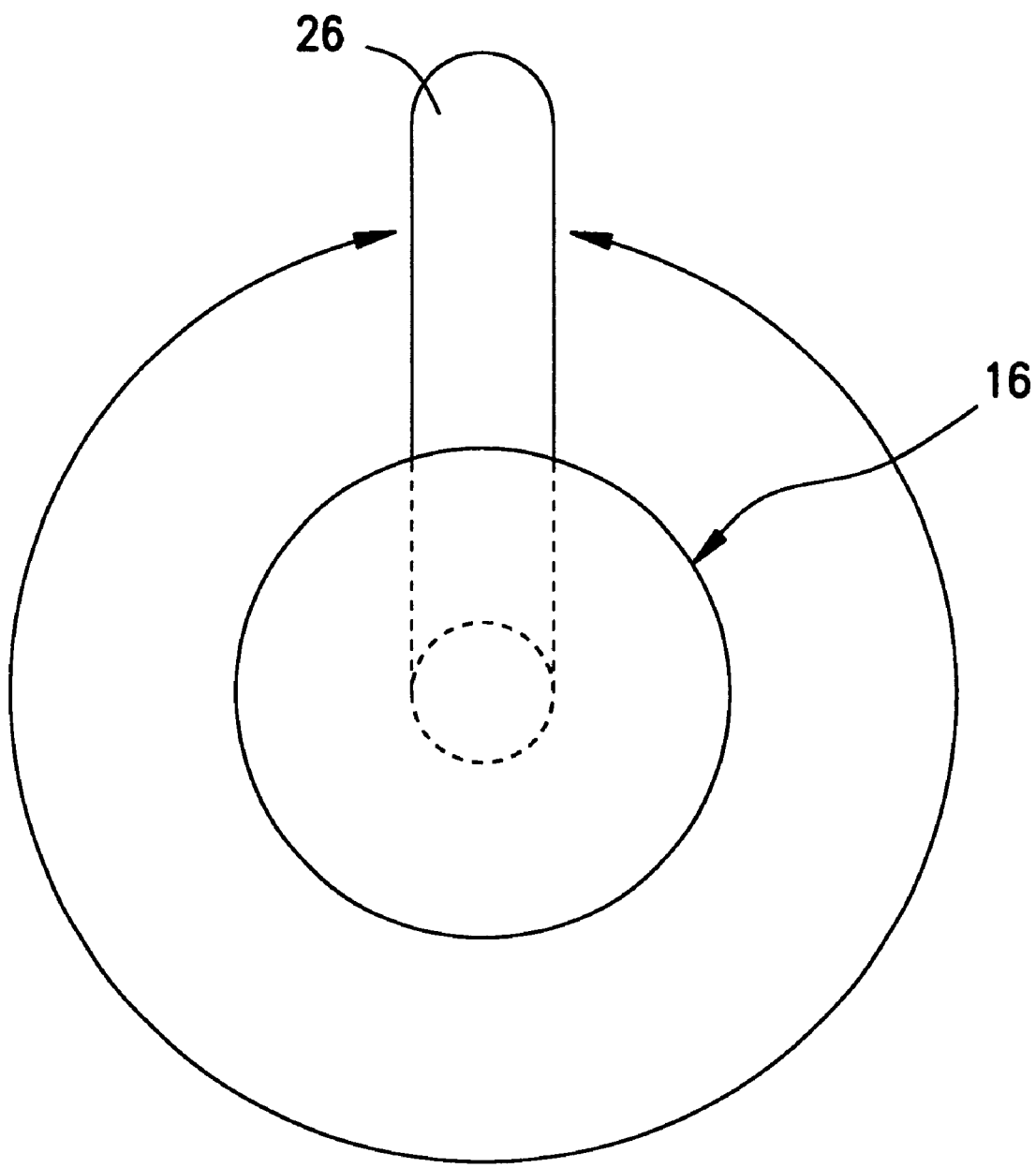
FIG. 4 illustrates an axial cross-sectional view of the macerator component of FIG. 1, in an activated position.

In an activated position shown in FIG. 1, the core wire 12 has an arc such as is shown at 26. The core wire 12 is preformed to have the arc 26. The arc 26 acts as a macerator or clot disrupter when positioned and moved within a thrombus. In one embodiment, the macerating arc 26 is positioned within a thrombus and is moved so that the arc 26 is rotated such as is shown in cross-section in FIG. 4. By rotating the arc 26 over a radial distance of up to 360 degrees, the thrombus is scraped and disrupted within a blood vessel. The arc 26 may also be moved transversely through a clot. In one other embodiment, the arc 26 is moved radially and transversely in order to more completely disrupt the thrombus. One purpose of the scraping and disruption is to increase the surface area of the thrombus that is subsequently or concurrently exposed to lytic drugs. The lytic drugs are, in one embodiment, administered through an EHIC catheter 50, illustrated in FIG. 5a or 110, illustrated in FIG. 5 or 100 in FIG. 5b.

Figure 8:
FIG. 8 illustrates a side view of one embodiment of the core wire wherein the core wire distally comprises two arc shapes.

While a single arc 26 is shown, it is contemplated that the core wire 12 may preformed into multiple arcs such as is shown at 80 in FIG. 8. The amplitude of the arc 26 is preformed to be compatible to dimensions of a thrombus.

In one embodiment, the core wire 12 is made of an elastic material such as a super elastic Nitinol. Other materials with a degree of stiffening that permits their passage through a blood vessel, particularly biocompatible materials which have a memory and which are capable of returning to a first arc shape after having been straightened, are suitable for use as the core wire 12.

Figure 2:
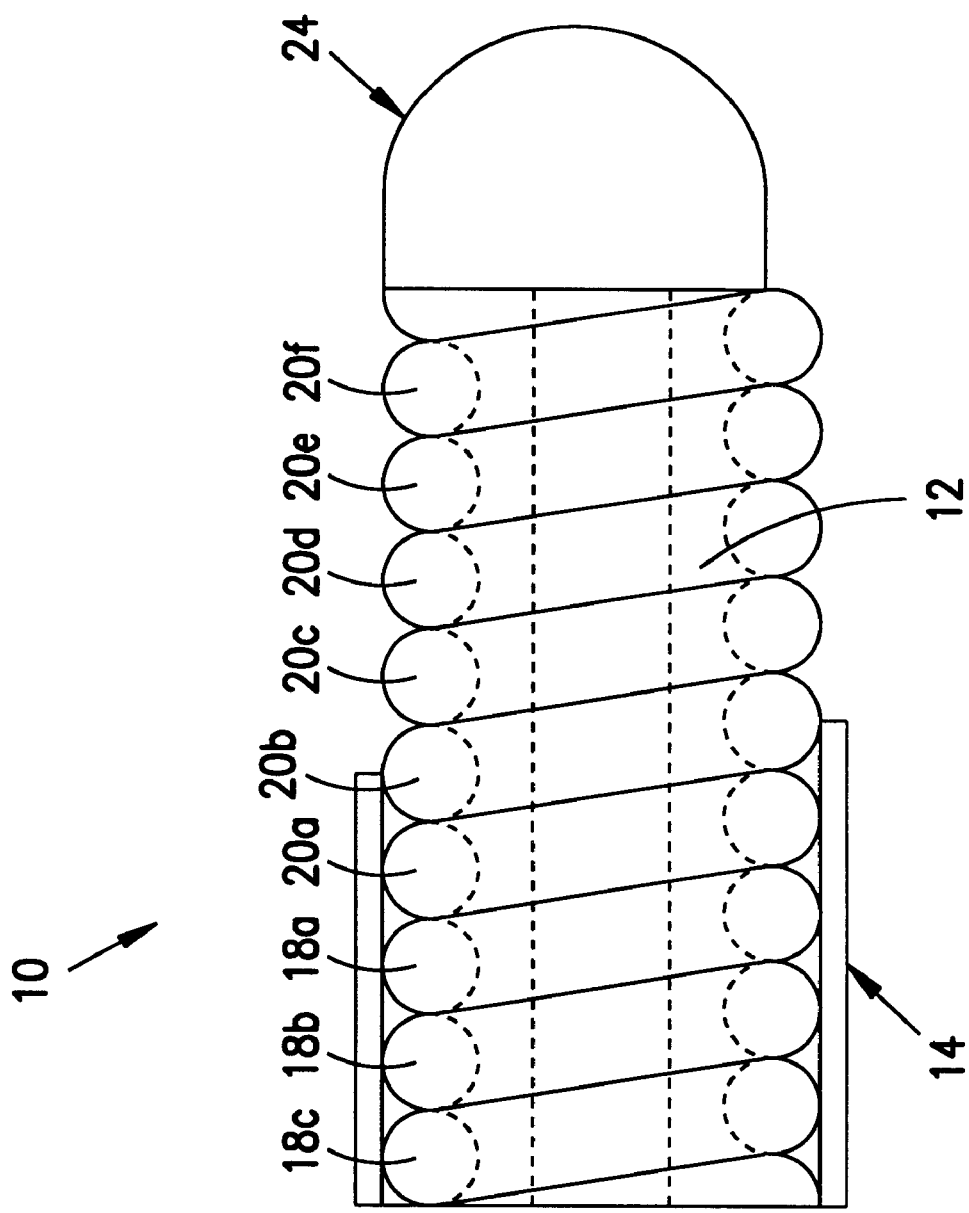
FIG. 2 illustrates a side view of the thrombus macerator of the present invention with the macerator component in an unexpanded, inactive position.

The core wire 12 is retractable within 14 to an inactive, arc-free shape by pulling the core wire 12 at a proximal end of the wire to change the symmetry from the arc 26 to a straightened segment such as is shown in FIG. 2. As the core wire 12 is straightened, the catheter portions 14 and 16 come together.

Figure 3A:
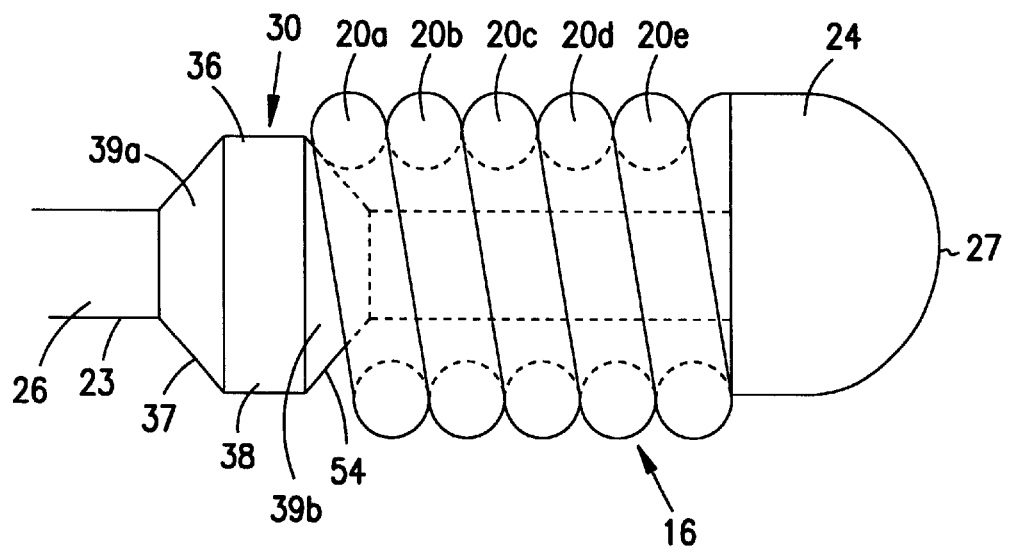
FIGS. 3a and 3b illustrate a side view of the thrombus macerator illustrating, with particularity, a stop mechanism.

In one other core wire embodiment, illustrated at 30 in FIG. 3a, a stop mechanism 36 is formed integrally with a core wire portion 26. The core wire 26 is positioned within the proximal catheter portion 14 and the distal catheter portion 16. The core wire portion 26 terminates at distal end 27 in an endcap 24. The distal catheter portion 16 encloses the core wire portion 26 and is adhered to the endcap 24 at coil 20f. The distal catheter portion 16 is also attachable to the stop mechanism 36 at coil 20a. The coil 20a is fused or is otherwise adhered to the stop mechanism 36 that is integral with the core wire 26.

The stop mechanism 36 comprises a main body 37 that defines a stopping surface 38. The main body 37 has a larger diameter than the diameter of the core wire portion 26. The stop mechanism 36 also includes a pair of opposing tapering surfaces 39a and 39b, respectively, that are positioned between the stopping surface 38 and the core wire portion 26.

Figure 3B:
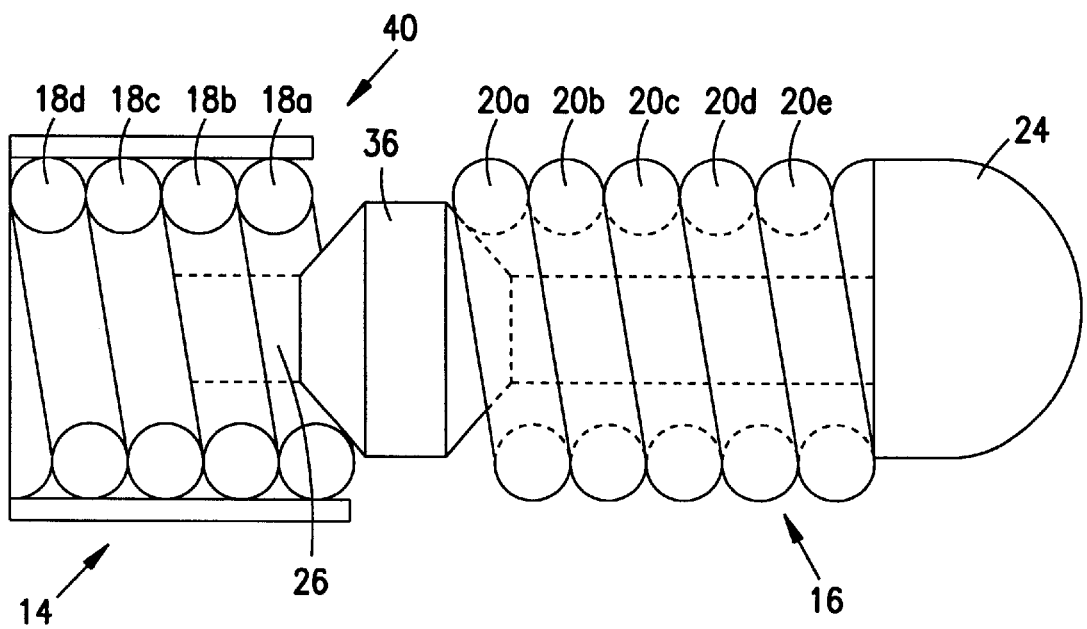

With this embodiment, as the core wire portion 26 is retracted, thereby straightening the wire portion 26, the retraction stop 36 seats or wedges into a lumen 40 of the distal catheter body portion 14 at the stopping surface 38, which is illustrated in FIG. 3b. The presence of the stop 36 facilitates transmission of torque between the distal catheter body portion 16 and the proximal catheter body portion 14 as the two independent coiled segments 18a–d and 20a–e are locked together. The locking occurs when the coil wire segments 18a and 20a are both seated on the same stop 36.

Figure 5:
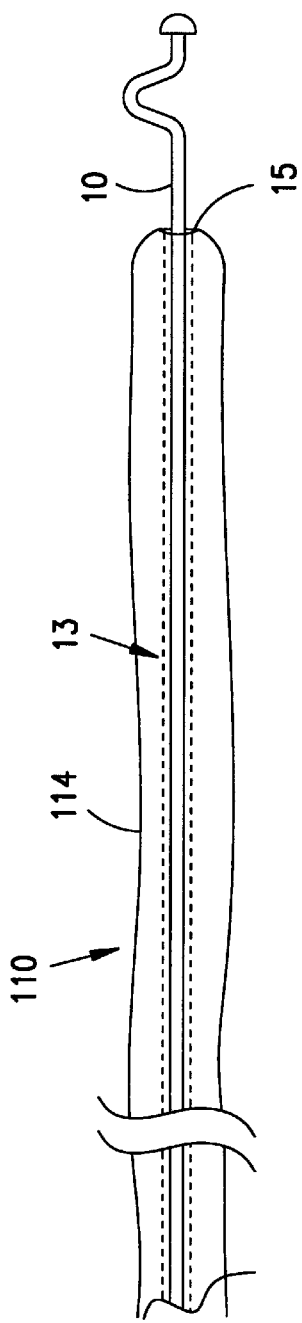
FIG. 5 illustrates a side view of one embodiment of an end hole infusion catheter with the macerating component of the present invention.
Figure 5A:
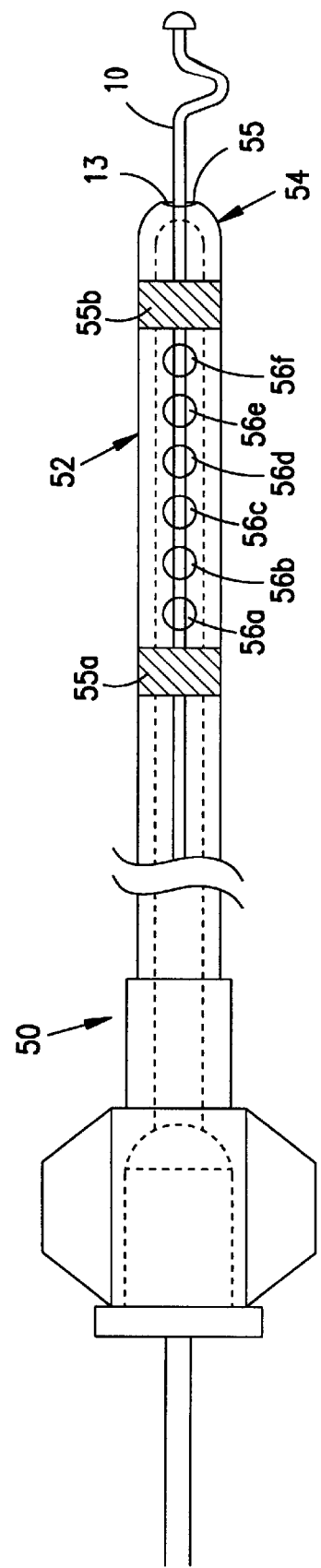
FIG. 5a illustrates a side view of one embodiment of an infusion catheter with the macerating component of the present invention.
Figure 7:
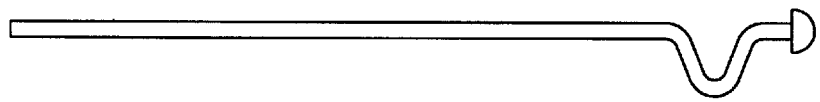
FIG. 7 illustrates a side view of one embodiment of the core wire wherein the core wire distally comprises a first arc shape.

In one embodiment illustrated in FIG. 5, the catheter 10 is passed through a lumen 13 and endhole 15, defined by the distal portion 114 of an endhole infusion catheter, EHIC, 110. The catheter 10 is passed by manually pushing the core wire 12 through the catheter 110 at a proximal end of the catheter 10, wherein the proximal end is not shown and out by way of the endhole 15.

In another embodiment illustrated in FIG. 5a, the catheter 10 is passed through a lumen 52 and endhole 55 of an end hole infusion catheter 50 that also defines sideholes 56a, 56b, 56c, 56d, 56e and 56f for drug delivery. A core wire such as the core wire 12 may also be pushed through the catheter 50. A marker band may be applied on the distal endcap 24. The marker band is used for positioning and confirming movement of the core wire 12. The marker band is comprised of a radiopaque material such as gold, tungsten, tantalum and the like.

The EHIC catheters 50 and 110 may be of varying size, including a microcatheter size. The EHIC catheters 50 and 110 may be duel lumen catheters, shown in cross-section in FIGS. 5d1 and 5d2, with lumens 19 and 21. The EHIC catheters 50 and 110 may also be single lumen catheters, as shown at 23 in FIG. 5c.

Thrombi are most effectively lysed when the drug actually comes into contact with the largest possible surface area of a thrombus. It is believed that the EHIC catheters, acting in concert with the thrombus macerating microcatheter of the present invention, produces a synergistic effect by the combined action of local drug delivery and mechanical thrombus disruption.

In one embodiment illustrated in FIG. 5b, the catheter 10 is transported to a treatment site within a catheter such as the catheter 110. In one other embodiment, such as is illustrated for catheter 100, a proximal main body portion 38 is attached to the catheter 100. The distal main body portion 34 is positioned over the wire 26. The wire 26 defines the stop mechanism 36.

One other embodiment of the present invention is illustrated generally at 60 in FIGS. 6a and 6b. The guidewire 60 includes an elongate tubular shaft 70 formed of a material such as stainless steel or Nitinol hypodermic tubing. A distal end 72 is formed of coil segments 74 and 76. The coiled segment 74 is attached to the tubular shaft 70. The coiled segment 76 is attached to a cap 66 of a core wire 61. The core wire 61 extends through the elongate tubular shaft 70. The core wire 61 is, in one embodiment, made of an elastic material such as Nitinol. The core wire 61 and the core wire 12 may be coated with a material such as TEFLON, or may be coated with an anti-thrombic material or hydrophilic coatings.

The core wire 61 as shown in FIG. 6b, forms an arc 62. The arc 62 may be positioned within a thrombus in order to treat the thrombus as described above. The core wire 61 terminates in the cap 66. In one embodiment, the core wire also includes the stop mechanism 36.

Figure 9:
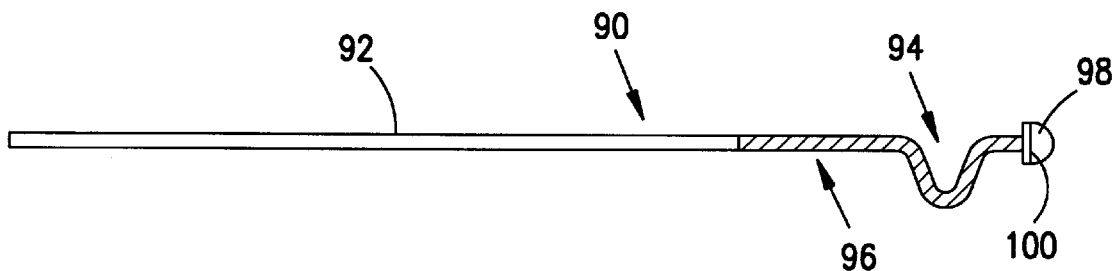
FIG. 9 illustrates a side view of one embodiment of a conventional guidewire of the present invention.

In a guidewire embodiment, illustrated generally at 90 in FIG. 9, the steerable guidewire 90 includes a proximal wire portion 92, a distal wire arc portion 94 formed within distal coil segment 96. The guidewire 90 terminates distally in an endcap 98. The wire acts within a catheter to cover and straighten the arc portion 94 during advancement. As the distal end of the wire exits the catheter, the wire arc portion 94 is allowed to expand.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the preset invention. Accordingly, the present invention is not limited in the particular embodiments which have been described and detailed therein. Rather, reference should be made to the appended claims as indicative of the scope and content of the present invention.

What is claimed:

1. A thrombus disrupting device, comprising:

a main body comprising a coil defining a lumen comprising a distal end portion;

a single wire comprising an elastic material, positioned within the lumen and extending from the lumen, the wire comprising a distal end; and a main body segment positioned over the wire, proximal to the distal end of the wire and distal to the main body wherein the wire has a first arc conformation wherein the main body segment is separated from the main body and a second arc-free conformation wherein the main body segment contacts the main body.

2. The thrombus disrupting device of claim 1 wherein the main body segment is comprised of a coil.

3. A thrombus disrupting device comprising an elongated tubular main body, a tubular body segment separable from the elongated main body, and a single wire having a distal end, positioned within the tubular main body and the tubular body segment, and an endcap positioned at the distal end of the wire and the tubular body segment, wherein the wire, in a first position wherein the tubular body segment is separated from the main body, has an exposed portion which is not positioned in either of the tubular body segment or the tubular main body, wherein the exposed portion of the wire, in one position, defines an arc, wherein the arc is proximal to the distal end of the wire.

4. The thrombus disrupting device of claim 3 wherein the tubular main body distally terminates in coil segments.

5. The thrombus disrupting device of claim 4 wherein one of the coil segments is attached to an endcap of the core wire.

6. The thrombus disrupting device of claim 4 wherein one of the coil segments is attached to the tubular main body.

* * * * *